United States Patent
Gill et al.

(10) Patent No.: US 11,122,758 B2
(45) Date of Patent: Sep. 21, 2021

(54) GENETIC SYSTEM FOR PROMOTING RECOMBINATION AND GENE TRANSFER IN WHEAT

(71) Applicant: Kansas State University Research Foundation, Manhattan, KS (US)

(72) Inventors: Bikram S. Gill, Manhattan, KS (US); Bernd Friebe, Manhattan, KS (US); Dal-Hoe Koo, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/339,212

(22) PCT Filed: Oct. 7, 2017

(86) PCT No.: PCT/US2017/055608
§ 371 (c)(1),
(2) Date: Apr. 3, 2019

(87) PCT Pub. No.: WO2018/067977
PCT Pub. Date: Apr. 12, 2018

(65) Prior Publication Data
US 2020/0037566 A1 Feb. 6, 2020

Related U.S. Application Data

(60) Provisional application No. 62/405,375, filed on Oct. 7, 2016.

(51) Int. Cl.
*A01H 5/10* (2018.01)
*A01H 6/46* (2018.01)

(52) U.S. Cl.
CPC ............ *A01H 6/4678* (2018.05); *A01H 5/10* (2013.01)

(58) Field of Classification Search
None
See application file for complete search history.

(56) References Cited

U.S. PATENT DOCUMENTS

| | | |
|---|---|---|
| 6,407,311 B1 | 6/2002 | Feldman et al. |
| 8,487,167 B2 | 7/2013 | Morris et al. |
| 2009/0031444 A1 | 1/2009 | Wittich et al. |
| 2016/0251668 A1 | 9/2016 | Gill et al. |

FOREIGN PATENT DOCUMENTS

| WO | 2016116032 | 7/2016 |
|---|---|---|

OTHER PUBLICATIONS

Martinenz-Perez et al .Journal of Cell Science (1999) 112:1761-1769.*
Endo et al .Journal of Hered. (1996):87:295-307.*
Lui et al (Chromosome Res (2011)19:669-682.*
Qi, et al., "Homoeologous recombination, chromosome engineering and crop improvement", Chromosome Research (2007)15:3-19.
International Search Report and Written Opinion in corresponding PCT/US2017/055608, dated Jan. 19, 2018.
Koo, et al.,"Homoeologous recombination in the presence of Ph1 gene in wheat", Chromosoma (Dec. 1, 2016) 126:531-540.
Friebe et al., "Development and identification of a complete set of Triticum aestivum—Aegilops geniculata chromosome addition lines1". Genome 42: 374-380 (1999).
Al-Kaff, et al., "Detailed dissection of the chromosomal region containing the Ph1 locus in wheat Triticum aestivum: with deletion mutants and expression profiling", Ann Bot. Apr. 2008;101(6):863-72.
Tiwari, et al., "Exploring the tertiary gene pool of bread wheat: sequence assembly and analysis of chromosome 5M (g) of Aegilops geniculata", Plant J., (Sep. 26, 2015);84(4):733-46.
Liu, et al., "Discovery and molecular mapping of a new gene conferring resistance to stem rust, Sr53, derived from Aegilops geniculata and characterization of spontaneous translocation stocks with reduced alien chromatin", Chromosome Res (2011) 19:669-682.

\* cited by examiner

*Primary Examiner* — Medina A Ibrahim
(74) *Attorney, Agent, or Firm* — Hovey Williams LLP

(57) ABSTRACT

Wheat lines comprising homoeologous pairing promoter genes from chromosome $5M^g$ from *Ae. geniculata* and methods of inducing homoeologous recombination in plant breeding from these lines.

23 Claims, 9 Drawing Sheets

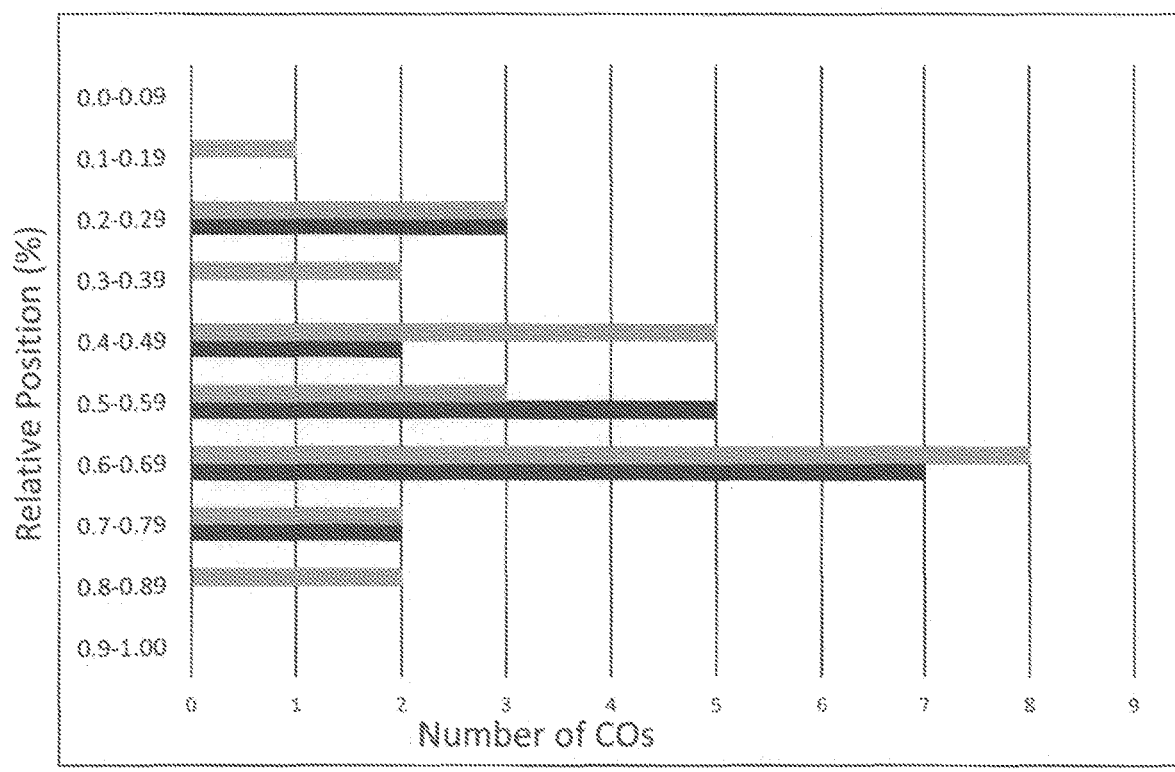
FIG. 10B
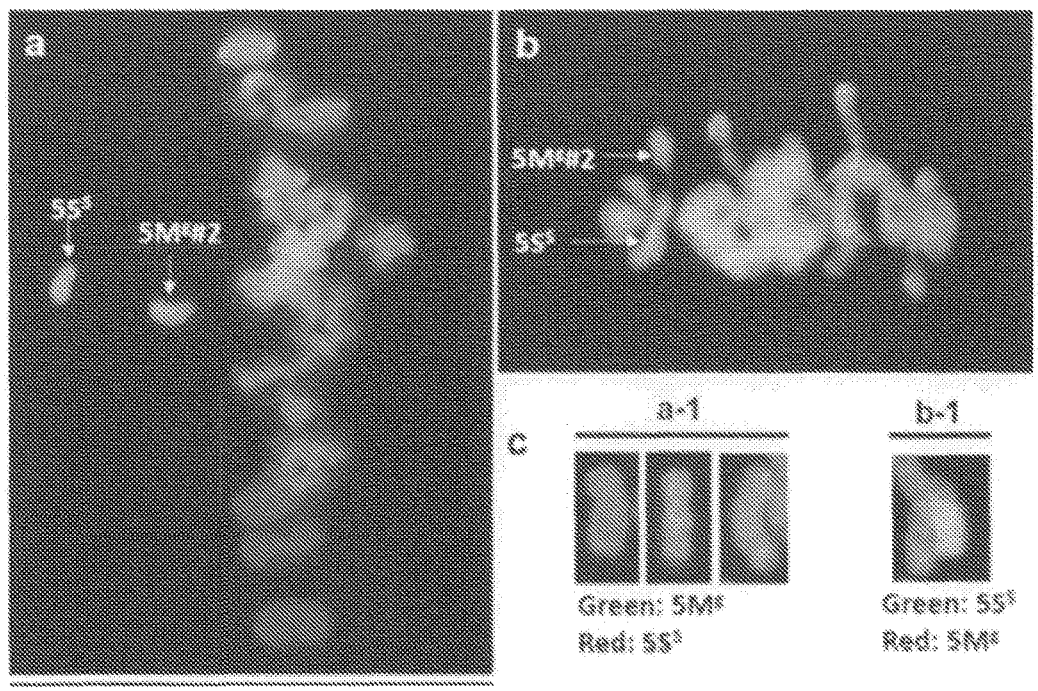
FIG. 11A-C

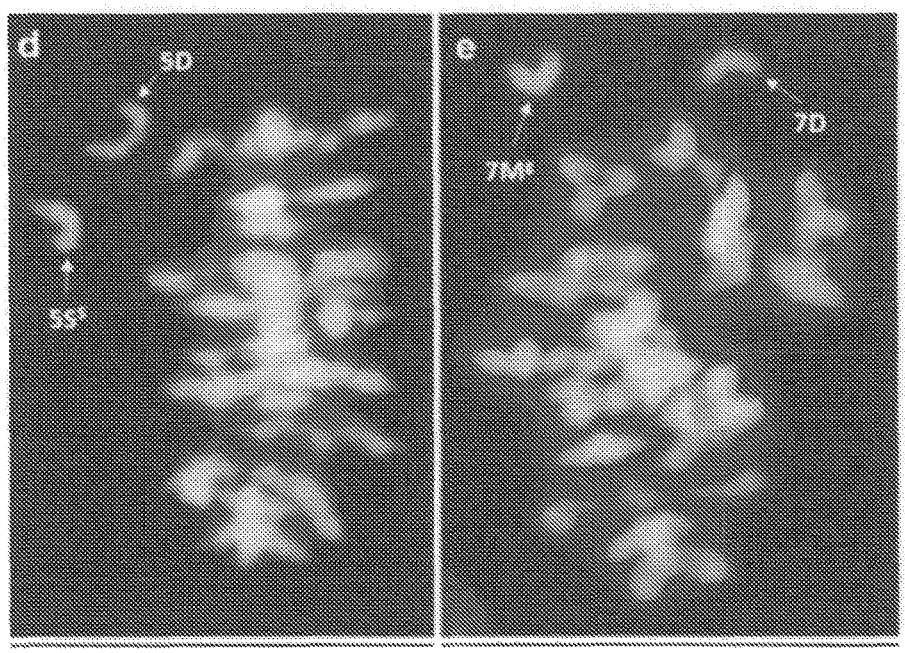
FIG. 11D-E
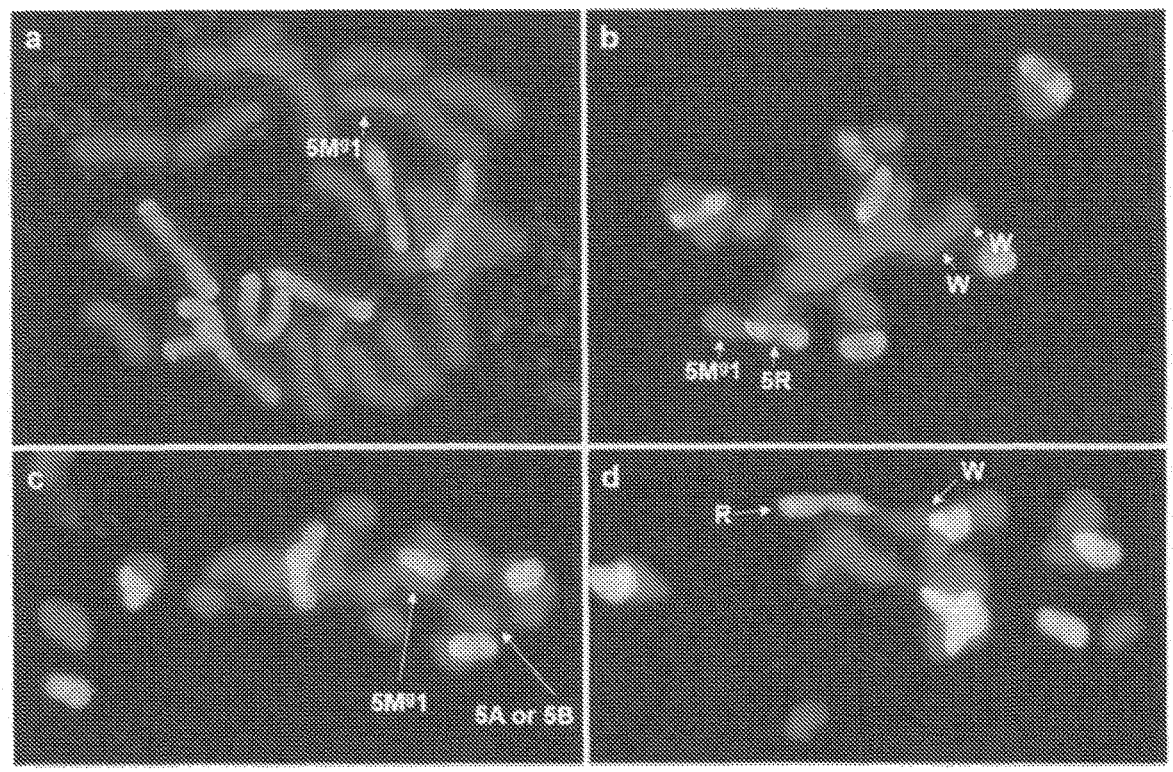
FIG. 12

GENETIC SYSTEM FOR PROMOTING RECOMBINATION AND GENE TRANSFER IN WHEAT

CROSS-REFERENCE TO RELATED APPLICATIONS

The present application is the U.S. National Stage of International Patent Application No. PCT/US2017/055608, filed Oct. 6, 2017, which claims the priority benefit of U.S. Provisional Patent Application Ser. No. 62/405,375, filed Oct. 7, 2016, entitled GENETIC SYSTEM FOR PROMOTING RECOMBINATION AND GENE TRANSFER IN WHEAT, each of which is incorporated by reference in its entirety herein.

BACKGROUND OF THE INVENTION

Field of the Invention

The present invention relates to new wheat genetic stocks for inducing homoeologous recombination events in wheat breeding, and methods and products relating to the same.

Description of Related Art

Pairing and recombination among homoeologous chromosomes in wheat and those of its wild relatives is tightly controlled by various genetic mechanisms. Two chromosomes are said to be "homeologous" or "homoeologous" when they are derived from two different genomes, but share characteristics such as similar nucleotide sequences, usually indicating some original ancestral homology, such that they are considered partially homologous. One gene locus, pairing homoeologous gene (Ph1), which resides on the long arm of chromosome 5B in *Triticum aestivum* and *Triticum turgidum*, exerts major control by preventing the pairing of homoeologous chromosomes (e.g., chromosome 1A pairing with 1B of wheat or pairing of 1B of wheat with 1R of rye). Ph1 is a dominant allele, such that a single functional copy is usually sufficient to prevent homoeologous pairing. Induced mutations in this gene, such as the recessive null mutation ph1b, interfere with the function of Ph1, such that homoeologous chromosomes can pair at variable (albeit extremely low) frequency and efficiency, resulting in crossing-over and exchange of genetic material. This process is referred to in the art as "homoeologous translocation" or "homoeologous recombination" (for crossovers from different species). Breeding lines containing ph1b or similar impaired Ph1 functions have been used to introduce into wheat chromosomes useful genes from chromosomes of related species. For example, when ph1b is in the homozygous condition, homoeologous pairing will occur (i.e., chromosome 1A can pair and recombine with 1B or 1D of wheat or 1R of rye). When alien chromosomes are present, recombination can occur between an alien chromosome and wheat homoeologues (i.e., wheat chromosomes 1A 1B or 1D can pair and recombine with 1R of rye) (or possibly even between an alien chromosome and alien homoeologues).

However, recombination frequencies using these approaches are notorious for being extremely low, with a 1% recombination frequency in resulting progeny being considered a high effective crossover event. Most crossover events have even lower frequencies of 0.001% or less. Thus, it will be appreciated that the process of introducing desired traits into wheat can be tedious and require numerous generations to achieve. There remains a critical need for improved approaches to induce higher order recombination among homoeologous chromosomes for the efficient production of wheat-alien recombinant chromosomes in wheat breeding techniques.

SUMMARY OF THE INVENTION

The present invention is broadly concerned with new wheat breeding methods and the development of a homoeologous pairing promotor (Hpp-5M$^g$) chromosome harboring promoter genes that enhance homoeologous pairing and crossover during breeding. *Aegilops geniculata* Roth is a tetraploid wild relative of wheat that has been studied as a source of disease and pest resistance traits. The sequence data for the full chromosome 5M$^g$ from *Ae. geniculata* is available from the Sequence Read Archive SRA database with accession number: SRX1167449, incorporated by reference herein. Sequence data from the 5M$^g$ short arm (5M$^g$S) is available from SRA with accession no: SRX474187, incorporated by reference herein. Chromosome 5 of *Ae. genculata* was originally under investigation because it also harbors genes for desirable resistance traits to be introduced into wheat. Three genes, Lr57 (leaf rust), Yr40 (yellow rust) and Sr53 (ug99) have been mapped on chromosome 5M$^g$ #2 of *Ae. geniculata* (TA10437), and a cytological marker (TR-14 repeat) for identifying 5M$^g$ chromosome have been reported in Tiwari et al., 84 *The Plant Journal* 733-746 (2015). See FIG. 1. It was unexpectedly determined that 5M$^g$ itself harbors promoter genes that can enhance homoeologous pairing and crossover (for other genes) during breeding when introduced into wheat backgrounds. Tiwari et al. also describe the sequence assembly and analysis of chromosome 5M$^g$, which is incorporated by reference in its entirety herein. Disomic substitution line DS5M$^g$(5D) (accession no: TA6675) described herein are maintained by the Wheat Genetics Resource Center at Kansas State University, www.k-state.edu/wgrc/.

Embodiments described herein concern a genetic system in wheat that promotes homoeologous recombination and negative interference leading to multiple recombination events per chromosome pair and, in addition, leads to recombination in proximal regions of chromosomes where recombination is highly suppressed, releasing previously inaccessible genetic variation for crop improvement programs. Hpp-5M$^g$-based chromosome manipulation is a new process and breeding scheme and has immediate application in wheat crop improvement programs. A breeding technique proving the utility of the method is demonstrated herein. We have shown that in plants, lacking the Ph1 gene (homozygous ph1b/ph1b) and having one dose of chromosome 5M$^g$, and one dose of wheat homoeolog 5D, the frequency of recombination between homoeologous chromosomes of wheat and alien species (in this case 5M$^g$ and 5D) is significantly increased. In addition, the work demonstrates clustering of multiple crossovers close to each other (negative crossover interference) and recombination events in proximal chromosome regions where recombination is usually suppressed. This work has multiple uses, including accessing agronomically-useful genes from wild relatives' genomes to enhance the genetic diversity of wheat; and enhancing the recombination potential for efficient breeding.

In one aspect, wheat plant genetic stocks or new wheat lines for inducing homoeologous recombination in plant breeding are disclosed. The wheat genetic starting stock comprises chromosome 5M$^g$ from *Ae. geniculata* and at least one chromosome bearing a pairing (Ph) gene which is not functioning. In some aspects, the plant comprises two ph1b mutant alleles.

Methods of inducing homoeologous recombination in wheat breeding are also described. The methods generally comprise crossing a wheat starting stock according to embodiments described herein with a source plant that comprises one or more target genes for recombination with one or more wheat chromosomes. Progeny from this cross is then selected with comprises a chromosome comprising one or more of the target genes transferred in a homoeologous recombination event during the crossing. Exemplary plants produced in accordance with the invention include Hpp-5M$^g$/5D, ph1b/ph1b.

Thus, described herein is a wheat genetic stock resulting from methods applied herein, Hpp-5M$^g$/5D, ph1b/ph1b for inducing homoeologous recombination in plant breeding, wherein the wheat genetic stock comprises chromosome 5M$^g$ from Ae. geniculata and two ph1b mutant alleles.

Seeds and wheat grain kernels produced according to the methods herein are also disclosed.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

and 5D. Nineteen recombinants (24.3%, n=78) were recovered. 5M$^g$ chromatin was visualized in green and 5D chromatin as red.

Figure 10A:
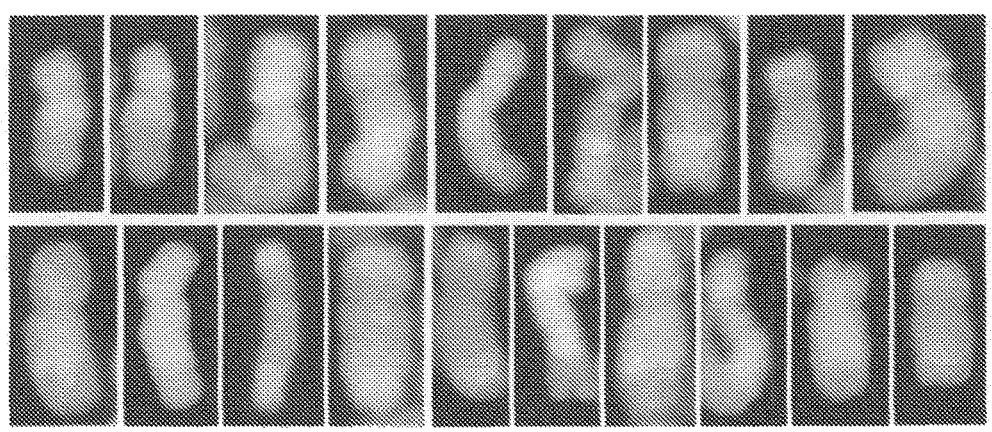
FIG. 10A shows images of recombinants recovered in the progeny of plants double monosomic for rec5M$^g$ #2 (R5)

FIG. 10B is a graph of the crossover distribution in recombinants derived from R5/5D (dark gray bars) and from 5M$^g$ #2/5D plants (light gray bars).

FIG. 11A-C shows images of homoeologous metaphase I pairing between chromosomes rec5M$^g$ #2 and 5S$^s$ of *Ae. searsii* (a and b), and recombinant chromosomes recovered in the progeny (c). a: 5M$^g$ #2 and 5S$^s$ univalents (91%); b: chiasmate association (9.0%) at MI; c: recombinants (6.7%, n=56) derived from homoeologous recombination of rec5M$^g$ #2 (visualized in green) and 5S$^s$ (visualized in red) in a-1 left, and vice versa in b-1 right.

FIG. 11D-E shows images of metaphase I pairing of plants double monosomic for chromosomes 5D and 5S$^s$ of *Ae. searsii*, no chiasmate association was observed (0.0%, n=120). e: meiotic metaphase I of plants double monosomic for chromosomes 7M$^g$ of *Ae. geniculata* and 7D of wheat showing univalent and very few chiasmate associations (0.4%, n=237).

FIG. 12 shows images of metaphase I pairing in a F$_1$ plant [DS5M$^g$ #1(5D)×*Secale cereale*, 2n=2x=14, RR]. a: mitotic chromosome constitution showing seven rye chromosomes (red), 20 A-, B-, and D-genome wheat chromosomes (blue), and one 5M$^g$ #1 chromosome (green); b: chiasmate association (1.5%, n=130) between chromosome 5M$^g$ #1 and chromosome 5R of rye; c: chiasmate association between chromosome 5M$^g$ #1 and a chromosome (5A or 5B) of wheat; d: chiasmate association (3.8%, n=130) between one rye chromosome and one wheat chromosome. W and R represent the wheat and rye chromosomes, respectively.

Figure 13:
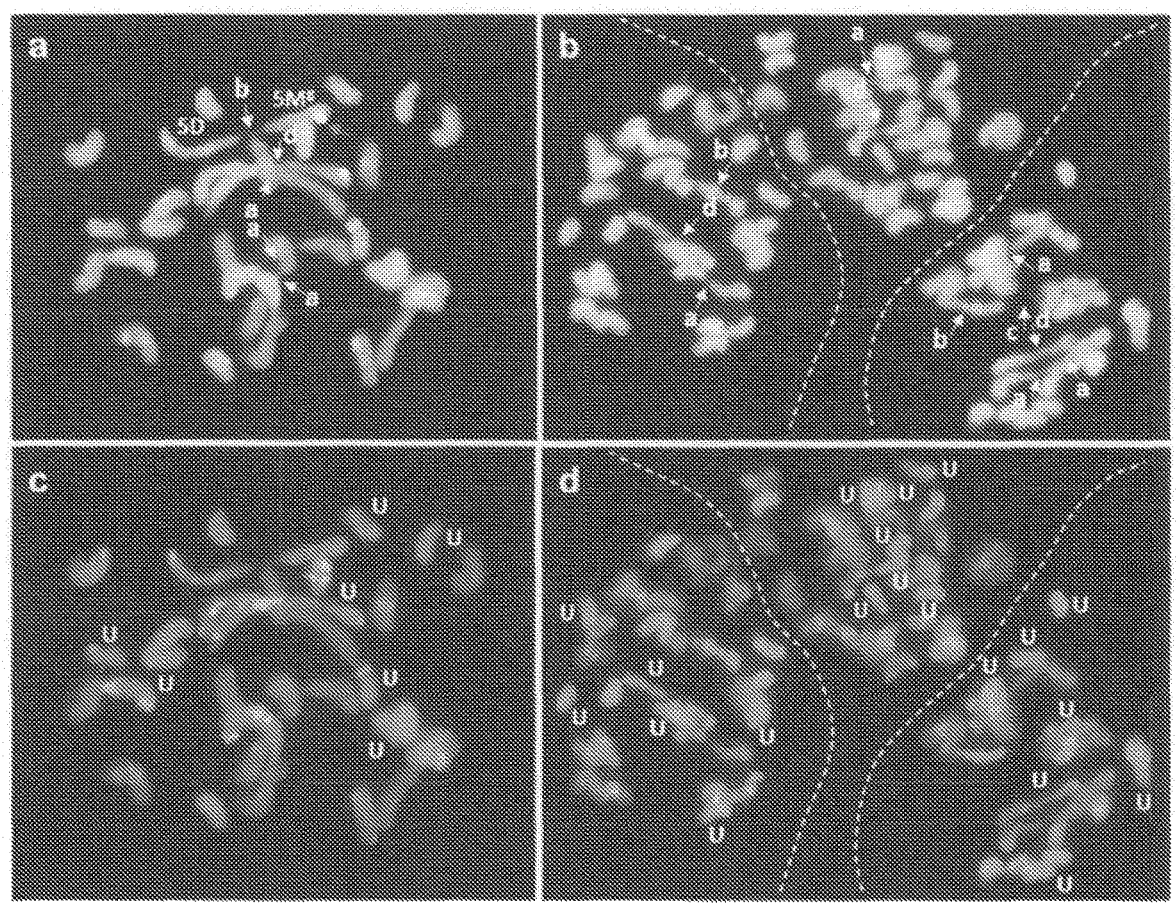

FIG. 13 shows images of homoeologous metaphase I pairing in the F$_1$ plants of (Chinese Spring wheat×*Ae. geniculata*). a-b: A-, B-, and U-genome chromosomes are visualized in blue and wheat D-genome and *Ae. geniculata* M-genome chromosome in red and green, respectively, in a and b. Sequential GISH/FISH using genomic DNA of *Ae. umbellulata* and the D-genome specific repetitive DNA probe pAs1 were used to identify U- and D-genome chromosomes (c-d). a: homoeologous metaphase I pairing between 5M$^g$ #1 and 5D (3.4%, n=114) (white signal marked by green arrow identifies repetitive DNA that is abundant in chromosome 5M$^g$ #1, unpublished). Four different types of chiasmate associations were identified type a: wheat-wheat (W-W), type b: wheat-M genome (W-M), type c: M genome-U genome (M-U), and type d: U genome-wheat (U-W).

Figure 14:
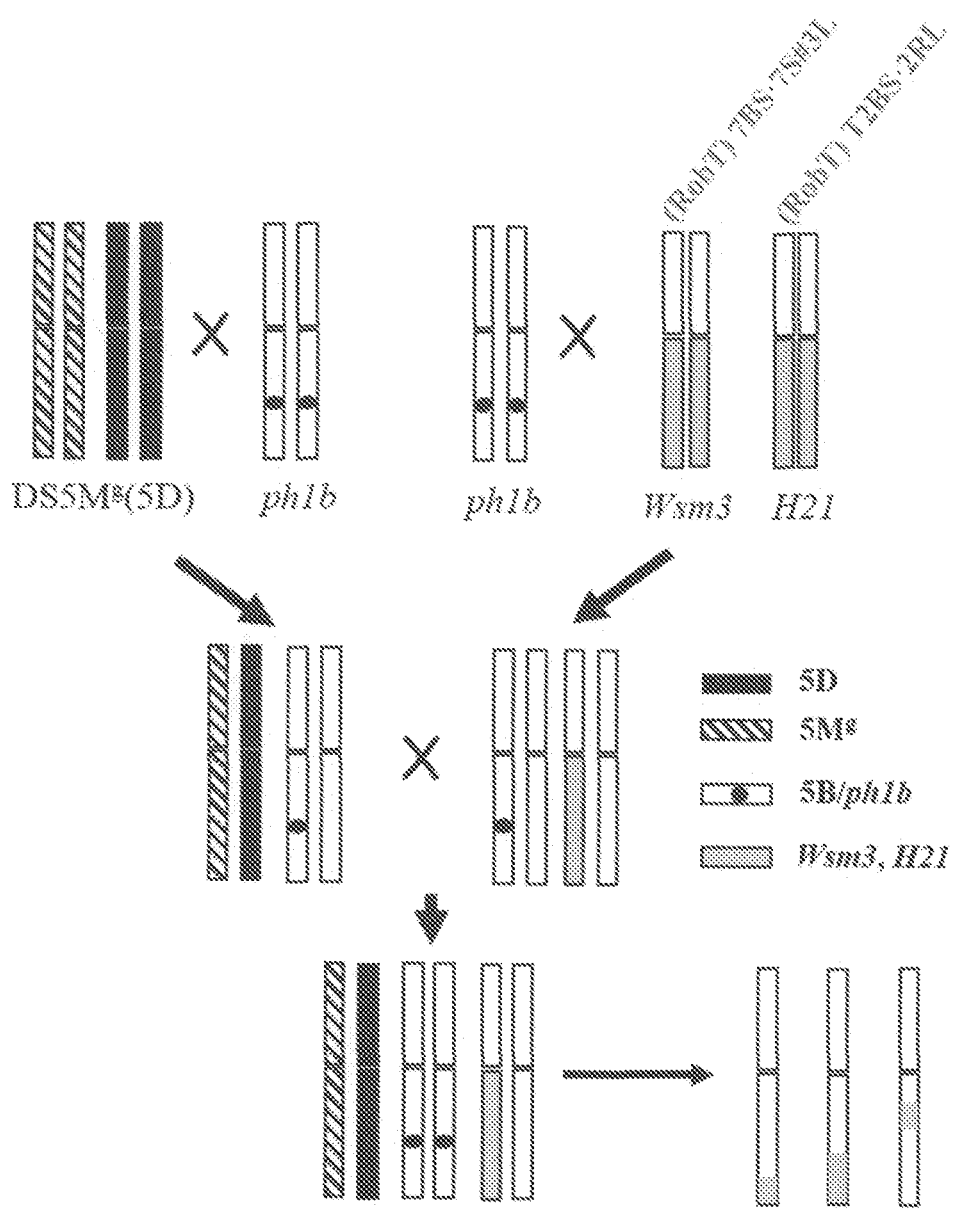

FIG. 14 illustrates a model for inducing homoeologous recombination between wheat and alien chromosomes in the presence of 5M$^g$ and absence of Ph1 (ph1b/ph1b). A wheat-alien substitution line is crossed with the ph1b mutant stock and then crossed with plants comprising 5M$^g$ and ph1b. Progeny plants heterozygous for the alien chromosome and for 5M$^g$ are selected.

DETAILED DESCRIPTION

Bread wheat, *Triticum aestivum* L., is a hexaploid species, 2n=6x=42, having seven A genome-, seven B genome-, and seven D genome-chromosome pairs. The A-, B-, and D-genome chromosomes are genetically related, however a gene on the long arm of chromosome 5B, (Ph1, Pairing homoeologous) ensures that only genetically closely related homologous chromosomes (1A with 1A, 1B with 1B, 1D with 1D) can pair and recombine, which results in a diploid inheritance. The process of chromosome segregation and recombination during meiosis produces genetic variation that forms the basis of plant and animal breeding programs for selection of superior cultivars or breeds for commerce. However, as noted above, the process of recombination is highly regulated to two to three events (called crossovers) per chromosome pair due to the phenomenon of interference (positive) and is usually restricted to distal regions of chromosomes. In addition, in interspecific hybrids where chromosomes are diverged (described as homoeologous chromosomes), recombination is usually suppressed and gene transfer may not be feasible.

The Triticeae tribe to which wheat belong contains several hundred species. The few species that are the direct ancestors of wheat have the same genomic composition as that of wheat (called primary gene pool). In the hybrids of primary gene pool species with wheat, the chromosomes of wheat and alien species can pair and undergo homologous recombination. However, the majority of alien species carry genomes different from wheat and form the tertiary gene pool. Gene transfer from distantly related species of the tertiary gene pool to wheat cannot be achieved normally by homologous recombination because the Ph1 gene on chromosome arm 5BL suppresses homoeologous recombination (allows only homologous chromosomes to pair and recombine) and hence gene transfer.

Interference with or deletion of Ph1 gene of wheat, such as in the mutant stock ph1b/ph1b, allows genetically more distantly related homoeologous chromosomes of wheat and other species (i.e., alien chromosomes) to pair and recombine permitting limited gene transfer. Thus, for example, 1A with 1B, or 1D, or 1R of rye, or 1H of barley, can pair and recombine. Currently, gene ph1b □induced homoeologous recombination is used to transfer agronomically important genes from species of the tertiary gene pool (they carry genomes other than the A, B or D genome of wheat) into cultivated wheat. However, the frequency of ph1b□induced homoeologous recombination is extremely low and is usually restricted to distal regions of chromosomes. The recombination is suppressed in proximal chromosome regions (those closer to the centromere) and genes located in these regions cannot be transferred by induced homoeologous recombination.

Described herein is chromosome 5M$^g$ from *Ae. geniculata* Roth (TA2899 or TA10437), which escapes the diploid pairing control and freely recombines with homoeologous 5D chromosomes of wheat in the presence of Ph1, even in proximal chromosome regions where recombination is usually suppressed. Furthermore, 5M$^g$ in the absence of a functional Ph1 dramatically enhances both the frequency as well as pattern of ph1b-induced recombination events for other chromosomes, including recombination in proximal chromosomal regions (close to the centromere). Thus, proximal regions of chromosome halves can recombine in resulting Hpp-5M$^g$/5D, ph1b/ph1b genotypes (progeny). Not only that, but normally the presence of one crossover suppresses the occurrence of another nearby as part of a phenomenon termed negative interference. However, in Hpp-5M$^g$/5D, ph1b/ph1b genotypes also this process breaks down and results in the clustering of several crossover or recombination events close to each other. This opens the possibility of producing wheat alien transfers with small alien segments and thereby reducing linkage drag cause by the presence of deleterious alien genes. This new strategy is described in detail herein.

It will be appreciated that this is a completely new system to induce homoeologous recombination between wheat and alien chromosomes and at a much higher level than possible previously. This strategy can revolutionize the transfer of alien genes from the tertiary gene pool, make it more efficient and allow also the transfer of alien genes that are located in proximal chromosome regions. The proposed strategy will also greatly impact wheat crop improvement by unlocking previously inaccessible regions of new genetic variation.

In the embodiments describe here, chromosome 5M$^g$ transferred from *Ae. geniculata* into wheat harbors homoeologous recombination promotor gene(s) that increase the frequency of homoeologous recombination between chromosomes of wheat and alien species, especially when combined with genotypes lacking a functional Ph1 gene. In addition, the system allows for the clustering of multiple crossovers close to each other apparently due to a gene(s) that promotes negative crossover interference. Furthermore, recombination events can also occur in proximal chromosome regions where recombination is usually suppressed. These are completely new findings in the field of biology and can be used to produce new genetic variation, which could not be done with existing methods.

In one or more embodiments, new wheat starting lines or genetic stocks are described, which can be used to induce and enhance homoeologous recombination events in plant breeding. Thus, the starting lines are preferably capable of serving as a parent for breeding stable wheat cultivars. The wheat starting stock comprises at least a portion of chromosome 5M$^g$ from *Ae. geniculata* and at least one chromosome bearing a pairing (Ph) gene which is not functioning. Preferably, the entire 5M$^g$ chromosome has been introduced into the starting stock line; however, it will be appreciated that recombinant versions of the chromosome may be sufficient provided that the chromosome retains one or more native homoeologous pairing promotor gene(s) from 5M$^g$ of *Ae. geniculata*. For example, in some cases, introduction of 5M$^g$ into the wheat background line yields one or more translocated wheat genes in distal regions of the transferred 5M$^g$ chromosome in the starting stock. Such lines may nonetheless be suitable for use in the invention. In the wheat starting stock, 5M$^g$ pairs with wheat 5D chromosome. Preferably, the wheat starting stock is heterozygous for 5M$^g$/5D. The wheat starting stock includes a non-functioning Ph gene, and preferably comprises the mutant homoeologous-pairing allele ph1b; however, it is appreciated that other approaches may be used to interfere with the native function of Ph1 in the starting stock. In one or more embodiments, the starting stock is heterozygous for the alleles Ph1/ph1b. The starting stock wheat plant is preferably based upon a *Triticum aestivum* background; however, other wheat species may be used. In one or more embodiments, the starting stock is the progeny from crossing disomic substitution line DS5M$^g$(5D) (accession no: TA6675) with a homozygous ph1b mutant line.

The starting stock can be used in traditional plant breeding techniques to enhance the frequency of recombination events during plant crossing. In one or more embodiments, methods for inducing homoeologous recombination in wheat breeding are described. The methods generally involve crossing the wheat starting stock with a plant that contains one or more target genes desired for introduction into the wheat line. The source plant containing one or more target genes desired for introduction include progeny from crossing a ph1b/ph1b mutant stock with wheat-alien introgression stock. A variety of plants (e.g., wheat-alien introgression stocks) may be used as the source for the target genes, so long as they are capable of crossbreeding with wheat, such as other cereals, grasses, etc. Exemplary source plants include other wheat or non-wheat lines harboring desirable traits. The source plant may be heterozygous or homozygous for the target gene. The source plant may include a functional Ph1 allele. The source plant may also include a chromosome bearing a pairing (Ph) gene which is not functioning, comprises the mutant homoeologous-pairing allele ph1b. The source plant may be heterozygous for Ph1/ph1b or homozygous for ph1b/ph1b.

During crossing one or more homoeologous chromosomes from each parental line pair up and one or more target genes is translocated from one chromosome to the other. The resulting progeny can be selected using conventional sorting techniques to identify progeny that comprises one or more of the target genes transferred into the progeny plant in a homoeologous recombination event during the crossing. The genes introduced via recombination may be alien genes resulting in one or more recombinant chromosomes in the progeny plant. In one or more embodiments, the target gene that is transferred during the recombination event may be one that is/was located proximally (i.e., near the centromere) of the chromosome. Alternatively, the target gene may be located on a distal region of the chromosome. Advantageously, the methods of the invention may involve two or more recombination events in a single cross. Thus, two or more genes may be transferred into the crossing of the parental plant lines.

It will be appreciated that progeny seed which expresses the one or more target genes can be collected and grown into plants likewise expressing the desired genes. Thus, progeny seeds and wheat grain kernels are also contemplated herein. The progeny plants are preferably heterozygous for chromosome 5M$^g$/5D, and homozygous for ph1b. Thus, it will be appreciated that the progeny can itself be used to propagate additional recombination events through subsequent breeding generations. The 5M$^g$ chromosome is preferably stably incorporated into the new wheat lines. Thus, progeny such as Hpp-5M$^g$/5D, ph1b/ph1b can be used to induce homoeologous recombination in plant breeding, where Hpp-5M$^g$/5D, ph1b/ph1b comprises chromosome 5M$^g$ from *Ae. geniculata* and two ph1b mutant alleles. The Hpp-5M$^g$/5D, ph1b/ph1b genetic lines are demonstrated as giving rise to significantly improved breeding outcomes when subsequently crossed with other plants (leading to additional recombination events).

Methods of the invention involving the 5M$^g$ introduced into the wheat background permit a much higher rate or frequency of successful recombination events with each crossing or propagation step. That is, in one or more embodiments, the frequency of a successful recombination of the target gene is preferably at least about 2% and more preferably at least about 4%, depending upon the locus of the gene to be transferred (where distal genes have a higher recombination frequency). It will be appreciated that such frequencies of achieving a successful recombination event are orders of magnitude higher than achieved with prior breeding techniques. In one or more embodiments, the frequency of recombination events in crossing the parental lines according to the invention is at least twenty-five times greater than recombination of the target gene when crossed with a wheat starting stock (such as ph1b/ph1b mutant stock) in the absence of the 5M$^g$ chromosome, and preferably at least about fifty times higher.

The approaches described herein can be used to introduce a variety of desirable traits into wheat. Examples of desirable traits that can be transferred via a recombination event into the progeny plants include rust resistance, mildew resistance, and the like.

Additional advantages of the various embodiments of the invention will be apparent to those skilled in the art upon review of the disclosure herein and the working examples below. It will be appreciated that the various embodiments described herein are not necessarily mutually exclusive unless otherwise indicated herein. For example, a feature described or depicted in one embodiment may also be included in other embodiments, but is not necessarily included. Thus, the present invention encompasses a variety of combinations and/or integrations of the specific embodiments described herein.

As used herein, the phrase "and/or," when used in a list of two or more items, means that any one of the listed items can be employed by itself or any combination of two or more of the listed items can be employed. For example, if a composition is described as containing or excluding components A, B, and/or C, the composition can contain or exclude A alone; B alone; C alone; A and B in combination; A and C in combination; B and C in combination; or A, B, and C in combination.

The present description also uses numerical ranges to quantify certain parameters relating to various embodiments of the invention. It should be understood that when numerical ranges are provided, such ranges are to be construed as providing literal support for claim limitations that only recite the lower value of the range as well as claim limitations that only recite the upper value of the range. For example, a disclosed numerical range of about 10 to about 100 provides literal support for a claim reciting "greater than about 10" (with no upper bounds) and a claim reciting "less than about 100" (with no lower bounds).

EXAMPLES

The following examples set forth methods in accordance with the invention. It is to be understood, however, that these examples are provided by way of illustration and nothing therein should be taken as a limitation upon the overall scope of the invention.

Example 1

Introduction

Meiotic recombination is central to evolution, speciation, plant breeding, and crop improvement. The meiotic recombination process is initiated by the formation of DNA double-strand breaks (DSBs) by the known protein, Spo11. Double-strand breaks are essential for promoting pairing and synapsis of homologous chromosomes in plants, fungi, and mammals Meiotic recombination results in the formation of cytological structures known as chiasmata at the sites of genetic crossovers. The formation of at least one chiasma between homologous chromosome pairs (the obligate genetic crossover) is essential for accurate chromosome segregation at the first meiotic division and genetic recombination.

Polyploid organisms with multiple sets of homoeologous chromosomes have evolved additional mechanisms for regulating homoeologous chiasmate metaphase I pairing (hereafter referred to as homoeologous metaphase I pairing) and genetic recombination. Pairing among homoeologous chromosomes must be suppressed and restricted to homologous chromosome pairs to ensure full fertility and fixing of hybrid vigor in polyploid organisms, a major advantage that preserves hybridity (homoeoloci heterozygosity). In hexaploid wheat, Triticum aestivum L. (genomes AABBDD, 2n=6x=42), homoeologous metaphase I pairing is accomplished by pairing homoeologous (Ph) genes, with Ph1 having the largest effect on homologous chiasmate metaphase I pairing (hereafter referred to as homologous metaphase I pairing). The A, B, and D subgenomes of wheat are closely related, but undergo strict homologous metaphase I pairing and only bivalents are observed at metaphase I (MI) of meiosis, resulting in diploid inheritance.

Two deletions of the Ph1 locus have been previously developed, ph1b in hexaploid wheat, and in ph1c in tetraploid wheat (genomes AABB, 2n=4x=28). In these mutants, homoeologous metaphase I pairing/recombination also occurs and occasional multivalents are observed. Two Ph1 candidate genes have been reported, namely cdc2 and C-Ph1. In addition to Ph1, a suppressor of homoeologous metaphase I pairing has been identified as Ph2, located on the short arm of chromosome 3D. Besides Ph1 and Ph2, a third suppressor has been detected on the short arm of chromosome 3A.

The ovate goat grass Aegilops geniculata Roth. is a tetraploid (2n=4x=28, $U^gU^gM^gM^g$) wild relative of bread wheat. Spontaneous hybrids between wheat and Ae. geniculata and the possibility of horizontal transgene escapes from cultivated to wild species have been reported. Meiotic metaphase I pairing analysis in wheat-Ae. geniculata hybrids revealed a low frequency of spontaneous wheat-Ae. geniculata chiasmate associations. Ae. geniculata is also an excellent source of resistance genes to various diseases and pests, and several genes have been transferred to wheat, including the leaf rust and stripe rust resistance genes Lr57 and Yr40, and the powdery mildew resistance gene Pm29. Chromosome $5M^g$, the source of Lr57 and Yr40 also harbors stem rust resistance gene Sr53, which is effective against stem rust races RKQQC and TTKSK (Ug99). A complete set of wheat-Ae. geniculata chromosome addition lines has been previously developed by Friebe et al. 1999, Genome 42: 374-380. In recent work, during the transfer of Sr53 into wheat, chromosome $5M^g$ freely recombined with chromosome 5D of wheat, even in the presence of Ph1. Described herein are techniques for induced homoeologous recombination, even in the presence of Ph1, due to the presence of homoeologous recombination promotor gene(s) on chromosome $5M^g$ of Ae. geniculata.

Materials and Methods

Plant Material and Chromosome Painting.

The cytogenetic stocks and hybrid plants used in this study are listed in the tables below.

TABLE 1

Cytogenetic stocks used for studying homoeologous recombination in wheat

| Accession | Chromosome number | Chromosome constitution | Description |
|---|---|---|---|
| NA | 42 | DS5M$^g$#1(5D) | One pair of 5D of wheat substituted by a pair of 5M$^g$#1 from Ae. geniculata, TA2899 |
| TA6675 | 42 | DS5M$^g$#2(5D) | One pair of 5D of wheat substituted by a pair of 5M$^g$#2 from Ae. geniculata, TA10437 |
| TA6561 | 42 | DS5S$^s$(5D) | One pair of 5D of substituted by a pair of 5S$^s$ from Ae. searsii |

TABLE 1-continued

Cytogenetic stocks used for studying homoeologous recombination in wheat

| Accession | Chromosome number | Chromosome constitution | Description |
|---|---|---|---|
| TA7659 | 44 | DA5M$^g$#1 | Addition of a pair of 5M$^g$#1 to Chinese Spring wheat |
| TA3517 | 42 | T7AS·7SS-7SL | One pair of wheat-*Ae. speltoides* translocation chromosome, involving 7AS of wheat and 7SS of *Ae. speltoides* substituting for chromosome 7A of wheat |

TABLE 2

Plant materials including F1 hybrids used for studying homoeologous recombination in Chinese Spring (CS) wheat

| Hybrid plant | Chromosome number | Description |
|---|---|---|
| P5M$^g$1 | 42 | F$_1$, DS5M$^g$#1(5D)/CS. Double monosomic for chromosomes 5D of wheat and 5M$^g$#1 of *Ae geniculata* |
| P5M$^g$2 | 42 | F$_1$, DS5M$^g$#2(5D)/CS. Double monosomic for chromosomes 5D of wheat and 5M$^g$#2 of *Ae geniculata* |
| R1 | 42 | F$_1$, Rec#14/CS. Recombinant Rec#14 recovered in the progeny of P5M$^g$2 |
| R2 | 42 | F$_1$, Rec#15/CS. Recombinant Rec#15 recovered in the progeny of P5M$^g$2 |
| R3 | 42 | F$_1$, Rec#7/CS. Recombinant Rec#7 recovered in the progeny of P5M$^g$2 |
| R4 | 42 | F$_1$, Rec#3/CS. Recombinant Rec#3 recovered in the progeny of P5M$^g$2 |
| R5 | 42 | F$_1$, Rec#3-1/CS. Recombinant Rec#3-1 recovered in the progeny of F$_1$ [Rec#3 x DS5M$^g$#2(5D)] |
| R6 | 42 | F$_1$, Rec#1/CS. Recombinant Rec#1 recovered in the progeny of P5M$^g$2 |
| F$_1$ [DS5M$^g$#2(5D)]/[DS5S$^s$(5D)] | 42 | Double monosomic for chromosomes 5M$^g$#2 and 5S$^s$ of *Ae. searsii* |
| F$_1$ [CS/DS5S$^s$(5D)] | 42 | Double monosomic for chromosomes 5D and 5S$^s$ |
| F$_1$ [DS5M$^g$#1(5D)/rye] | 28 | Haploid chromosome complement of wheat (minus 5D + 5M$^g$#1) and rye |
| F$_1$ (CS/Ae. geniculata) | 35 | Haploid chromosome complement of wheat and *Ae. geniculata* |
| F$_1$ [CS/DST7AS·7SS-7SL(7A)] | 42 | Double monosomic for T7AS·7SS-7SL and 7A |

Preparations of mitotic and meiotic chromosomes followed published protocols (Koo and Jiang 2009, Plant J. 59:509-516). Briefly, root tips were collected from plants and treated in a nitrous oxide gas chamber for 2 h. The root tips were fixed overnight in a 3:1 ethanol:glacial acetic acid and then squashed in a drop of 45% acetic acid. For meiotic chromosome preparations, anthers were squashed in 45% acetic acid on a slide and checked under a phase microscope. All slides were stored at −70° C. until use. The chromosome painting procedure was according to a previously published protocol (Zhang et al. 2001, Chromosoma 110:335-344). The genomic DNA painting probes used in this study are listed in the table below.

TABLE 3

Plant materials used in preparing the chromosome painting probes

| Species | Accession | Ploidy | Genome |
|---|---|---|---|
| *T. monococcum* | TA4342L96 | 2x | A |
| *Ae. speltoides* | TA1789 | 2x | S |
| *Ae. searsii* | TA2355 | 2x | S$^s$ |
| *Ae. tauschii* | TA2450 | 2x | D |
| *Ae. comosa* | TA2735 | 2x | M |
| *Ae. umbellulata* | TA1851 | 2x | U |
| *Secale cereale* | NA | 2x | R |
| *T. aestivum* | TA3008 | 6x | ABD |

Figure 3:
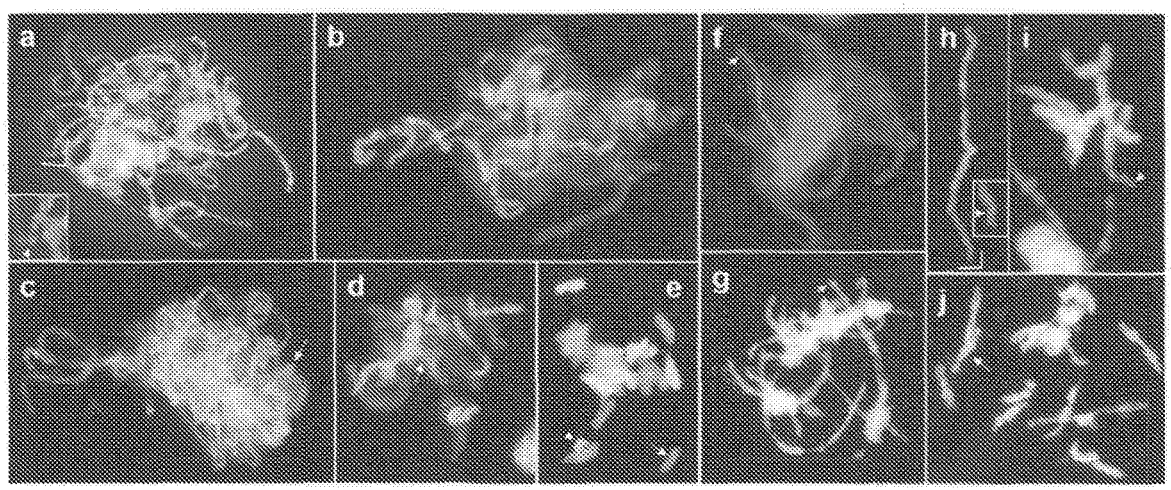
FIG. 3 shows images of synaptic association of homoeologous chromosomes (5M$^g$/5D) in meiotic prophase I of wheat plants double monosomic for chromosomes 5M$^g$ and 5D. a-b: complete synaptic association at mid-pachytene (a) and late-pachytene (b) between chromosomes 5M$^g$ #1 and 5D. The insert shows the GISH pattern of the distal region of homoeology of chromosomes 5M$^g$ #1(green) and 5D (Red); c-d: 5M$^g$ #1 univalent at mid-pachytene (c) and late-pachytne (d); e: 5M$^g$ #1 univalent (arrow) at late-diplotene; f: chromosome painting using total genomic DNA of Ae. comosa, the donor of the M genome of Ae. geniculata as a probe labeled with rhodamine and visualized in red fluorescence; (g): chromosome painting using total genomic DNA of Ae. comosa labeled with fluorescein and visualized with green fluorescence and total genomic DNA of Ae. tauschii, the D-genome donor of wheat, visualized in red fluorescence. Wheat chromosomes were counterstained with DAPI and fluoresce blue. Arrows in figs (f) and (g) point to the distal region of 5M$^g$ #2. h-j: complete synaptic association (94.6%) at mid-pachytene (h), late-pachytene (i), and mid-diplotene (j) between chromosomes 5M$^g$ #2 and 5D. The insert shows the distal region of chromosomes 5M$^g$ #2 and 5D. Note that the distal 4.7% of the long arm of 5M$^g$ #2 is derived from 5DL. Chromosome 5M$^g$ was labeled with fluorescein and fluoresces green, and the D-genome chromosomes were labeled with rhodamine and fluoresces red (except for fig. f). Chromosomes of the A and B genomes of wheat were stained with DAPI and fluoresce blue. Arrowheads in (h) and (i) point to the transition of the distal region of 5DL homology and the proximal homoeologous synapsis between 5M$^g$ #2 and 5D. Arrows in c, d, and e indicate 5M$^g$ #1 chromosomes and the arrowhead in (e) represents chromosome 5D of wheat.

Probes were labeled with either digoxigenin-11-dUTP or biotin-16-dUTP according to the manufacturer's instructions (Roche). Unlabeled total genomic wheat DNAs were used as a blocker. After post-hybridization washes, the probes were detected with Alexafluor 488 streptavidin (Invitrogen, Grand Island, N.Y.) for biotin-labeled probes, and rhodamine-conjugated anti-digoxigenin (Roche, Indianapolis, Ind.) for dig-labeled probes. Chromosomes were counterstained with 4',6-diamidino-2-phenylindole (DAPI) in Vectashield antifade solution (Vector Laboratories, Burlingame, Calif.). The images were captured with a Zeiss Axioplan 2 microscope using a cooled CCD camera Cool SNAP HQ2 (Photometrics, Tucson, Ariz.) and AxioVision 4.8 software (Carl Zeiss Microscopy LLC, Thornwood, N.Y.). The final contrast of the images was processed using Adobe Photoshop CS5 software. Chromosome measurements were done by Image J software.

association in 52.9% of pollen mother cells (PMCs) and stayed univalent in 47.1% of PMCs (n=87) (FIG. 3).

Figure 4:
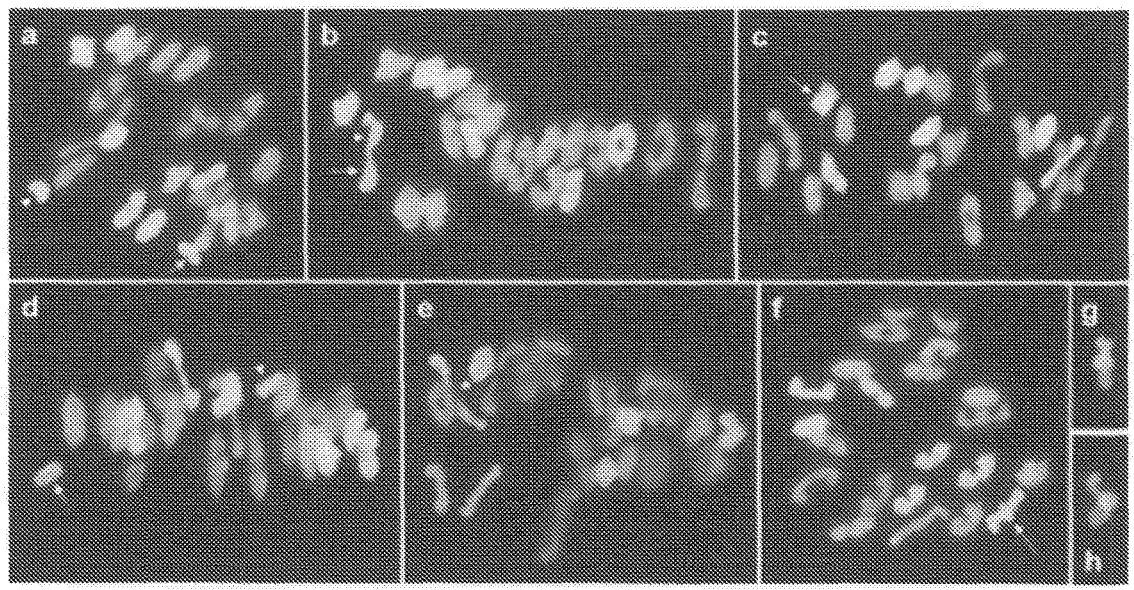
FIG. 4 shows images of homoeologous metaphase I pairing between chromosomes 5M$^g$ and 5D of wheat plants double monosomic for chromosomes 5M$^g$ and 5D. a: 5M$^g$ #1 (arrow) and 5D (arrowhead) as univalent (93.3%); b-c: rod and ring bivalents (6.7%) involving 5M$^g$ #1 and 5D; d: rec5M$^g$ #2 (arrow) and 5D (arrowhead) as univalents (16.7%); e-h: rec5M$^g$ #2/5D bivalent with terminal chiasmata (61.7%) (e), and proximal and interstitial chiasmata (f, g, and h) (21.7%). Note that proximal and interstitial chiasmata between chromosomes 5M$^g$ #1 and 5D were never observed.

GISH analysis at MI of P5M$^g$1 showed that the frequency of homoeologous metaphase I pairing between chromosomes 5M$^g$ #1 and 5D was 6.7% (n=130), whereas these chromosomes stayed univalent in 93.3% of PMCs (FIG. 4 and Table 4).

TABLE 4

Frequency of homoeologous pachytene synapsis, chiasmate pairing, and recombination involving wheat chromosome 5D with Ae. geniculata 5M$^g$ chromosomes, and the derived wheat-Ae. geniculata recombinant chromosomes R1 to R6

| Plant 5D (%)* | P5M$^g$10 | P5M$^g$2 L5 | R1 L19 | R2 L37 | R3 L50 | R4 L72 | R5 L5-S45 | R6 L5-L18 |
|---|---|---|---|---|---|---|---|---|
| Synapsis (%) | 52.9 (n = 87) | 94.6 (n = 56) | 90.6 (n = 39) | 93.8 (n = 64) | 98.1 (n = 52) | 97.5 (n = 40) | 100 (n = 55) | — |
| Chiasmata (%) | | | | | | | | |
| 5D-5M$^g$ | 6.7 | 21.7 | 4.8 | 2.8 | 1.5 | 0.8 | 22.9 | — |
| 5D-5D | | 61.7 | 90.4 | 97.2 | 97.8 | 99.2 | 73.0 | — |
| Univalent | 93.3 (n = 130) | 16.7 (n = 120) | 4.8 (n = 124) | 0.0 (n = 106) | 0.7 (n = 137) | 0.0 (n = 133) | 4.1 (n = 118) | — |
| HR (%)** | 10.0 (n = 110) | 24.8 (n = 106) | 4.1 (n = 74) | 2.0 (n = 50) | 0.0 (n = 73) | 0.0 (n = 50) | 24.3 (n = 78) | 4.0 (n = 100) |

—: Not determined
*Percent of 5D chromatin on 5 Mg
**Homoeologous recombination (HR) frequency determined by GISH in the progeny of each plant.

Results and Discussion

Figure 1:
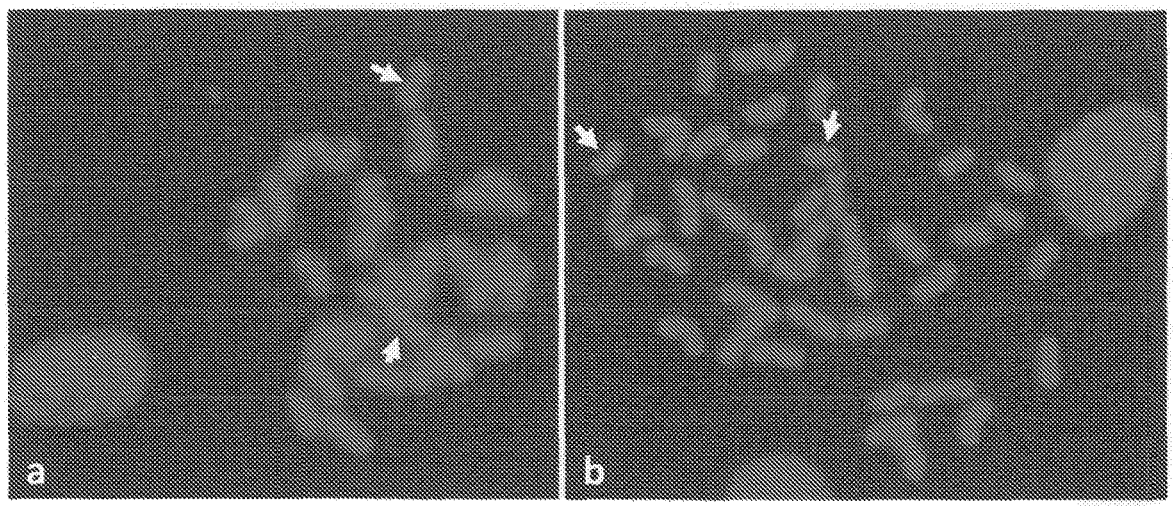
FIG. 1 shows images of chromosome 5M$^g$ specific localization of cytological marker TR-14 repeat, where the arrows indicate chromosome 5M$^g$ in (a) Ae. geniculata; and (b) disomic substitution line DS5M$^g$(5D).
Figure 2:
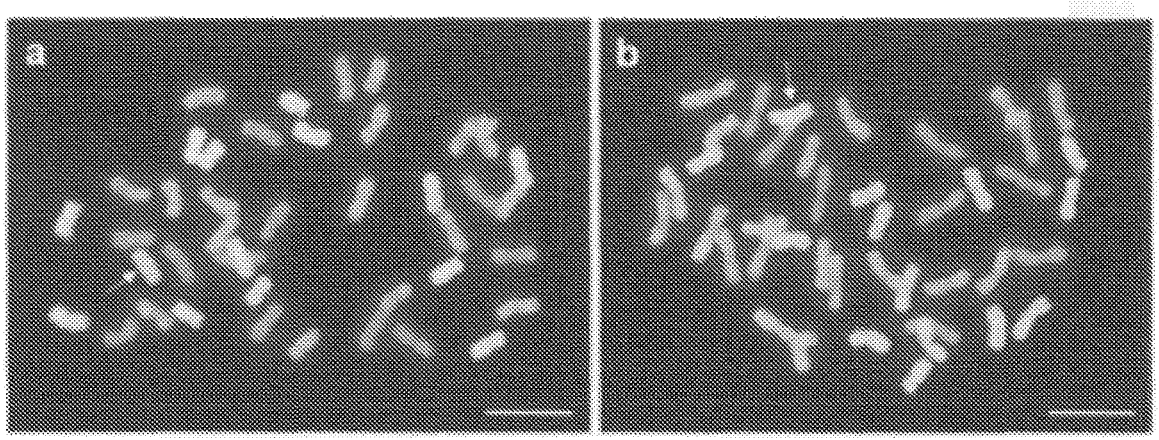
FIG. 2. shows images of GISH patterns of mitotic metaphase cell of plants (a) double monosomic for 5M$^g$ #1 and 5D; and (b) double monosomic for rec5M$^g$2 and 5D, labeled with genomic Ae. comosa DNA (green) and Ae. tauschii DNA (red). Arrows indicate the 5M$^g$ chromosome. Bars=10 μm.

Two 5M$^g$ #1 and 5M$^g$ #2 chromosomes from different Ae. geniculata accessions were used and isolated as disomic chromosome substitution lines DS5M$^g$ #1(5D) and DS5M$^g$ #2(5D) where 5D was substituted by 5M$^g$ (Table 1). To investigate the meiotic behavior of chromosomes 5M$^g$ and 5D, each of the two substitution lines was crossed with Chinese Spring (CS) wheat. The F$_1$ hybrids were double monosomic for 5M$^g$ and 5D, hereafter designated as P5M$^g$1 and P5M$^g$2 (Table 2). The chromosome constitution of each F$_1$ plant was confirmed by genomic in situ hybridization (GISH) using genomic DNA of Ae. tauschii Coss. (D-genome donor of wheat) to paint the D-genome chromosomes, including 5D, and genomic DNA of Ae. comosa Sm. in Sibth. & Sm. (the M-genome donor of Ae. geniculata) to paint chromosome 5M$^g$ (FIG. 2). Chromosomes 5M$^g$ #1 and 5M$^g$ #2 appeared to have maintained their structural integrity, as observed at mitotic metaphase during their isolation as additions to wheat (FIG. 2). However, pachytene analysis (see next section) indicated that although 5M$^g$ #1 was intact, the tip of the long arm of 5M$^g$ #2 was derived from the long arm of wheat chromosome 5D. Apparently, chromosomes 5M$^g$ #2 and 5D underwent one round of homoeologous pairing and recombination to produce the recombinant 5M$^g$ #2 chromosome, designated as rec5M$^g$ #2 hereafter, providing an opportunity to study the effect of terminal homology on homoeologous metaphase I pairing and recombination in P5M$^g$2 compared to the control P5M$^g$1.

Chromosome 5M$^g$ #1 Pairs and Recombines with 5D of Wheat in the Presence of pH1.

First, GISH analysis on pachytene chromosomes in P5M$^g$1 was used to investigate the synaptic association between chromosomes 5M$^g$ #1 and 5D. We considered only mid-pachytene or late-pachytene chromosomes as hybridization targets, because the stickiness of chromosomes prevented the differentiation of chromosomes 5M$^g$ #1 and 5D at zygotene and early pachytene stages. We observed that chromosomes 5M$^g$ #1 and 5D showed complete synaptic We observed seven 5M$^g$ #1/5D rod bivalents with end-to-end associations and one ring bivalent out of 130 PMCs analyzed (FIG. 4). These results demonstrated that chromosome 5M$^g$ #1 of Ae. geniculata recombined with 5D of wheat in the presence of Ph1.

Figure 5:
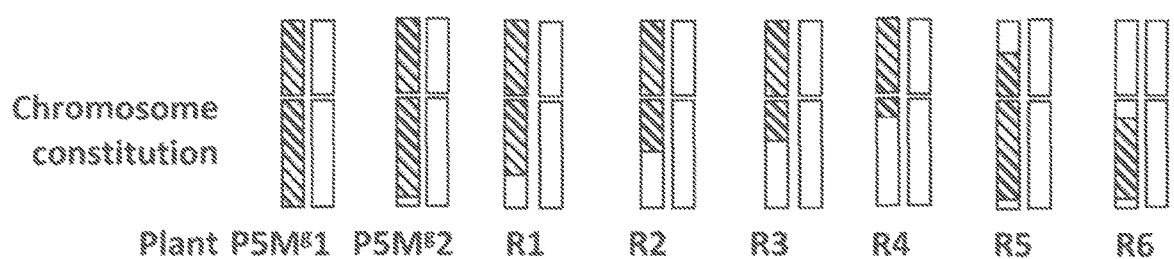
FIG. 5 illustrates the chromosome constitution and chiasmate pairing involving wheat chromosome 5D (white) with Ae. geniculata chromosomes 5M$^g$ #1 (hatch marks), 5M$^g$ #2, and the derived wheat-Ae. geniculata recombinant chromosomes R1 to R6, for the data presented in Table 4.

We then performed GISH analysis on mitotic metaphase chromosomes in the derived progenies, and identified 11 recombinants (10%) out of 110 plants analyzed (FIGS. 5, 6, and 7), confirming that homoeologous recombination between 5M$^g$ #1 and 5D occurred in the presence of Ph1.

Terminal Homology Between Chromosomes rec5M$^g$ #2 and 5D Promotes Synapsis and Increases Homoeologous Recombination Frequencies.

Two-color chromosome painting on pachytene chromosomes using a D-genome-specific probe labeled the terminal tip of the long arm of rec5M$^g$ #2, indicating that this region was actually derived from a D-genome chromosome, most likely from 5DL, and this chromosome was designated as rec5M$^g$ #2S•5M$^g$ #2L-5DL (FIG. 3f, g). The recombinant nature of rec5M$^g$ #2 was not detected by GISH of mitotic metaphase chromosomes because of the small size of the 5DL segment (FIG. 2b). Measurements of three complete pachytene cells revealed that the size of the 5DL segment was 4.7±0.5% of the long arm of rec5M$^g$ #2. This small segment possibly was acquired during the development of this genetic stock as a result of recombination between 5D and 5M$^g$ #2 as reported previously in hybrids between wheat and Ae. geniculata. On the contrary, no Ae. tauschii-derived chromatin was identified in chromosome 5M$^g$ #1 (FIG. 3a).

The synaptic association between rec5M$^g$ #2 and 5D was 94.6% (n=56) compared to 52.9% between 5M$^g$ #1 and 5D (FIG. 3 and Table 4). The overall metaphase I pairing between rec5M$^g$ #2 and 5D was 83.4% (Table 4). Two-color chromosome painting differentiated between homologous and homoeologous metaphase I pairing (FIG. 4). The frequency of homologous metaphase I pairing between 5D-5D was 61.7% (FIG. 4e). Surprisingly, we also observed metaphase I pairing in non-homologous interstitial and even proximal regions in 21.7% of PMCs (n=120) (FIG. 4f-h).

This frequency (21.7%) was approximately three-fold higher than that between of 5M$^g$ #1 and 5D (6.7%). No multivalents involving homoeologous wheat chromosomes were detected, indicating that homoeologous metaphase I pairing occurred only between 5M$^g$ and 5D. In addition, the majority of homologous chromosomes paired as ring bivalents with at least one chiasma per chromosome arm, which is similar to the metaphase I pairing observed in plants without chromosome 5M$^g$, suggesting that the effect of 5M$^g$ is localized.

Figure 6:
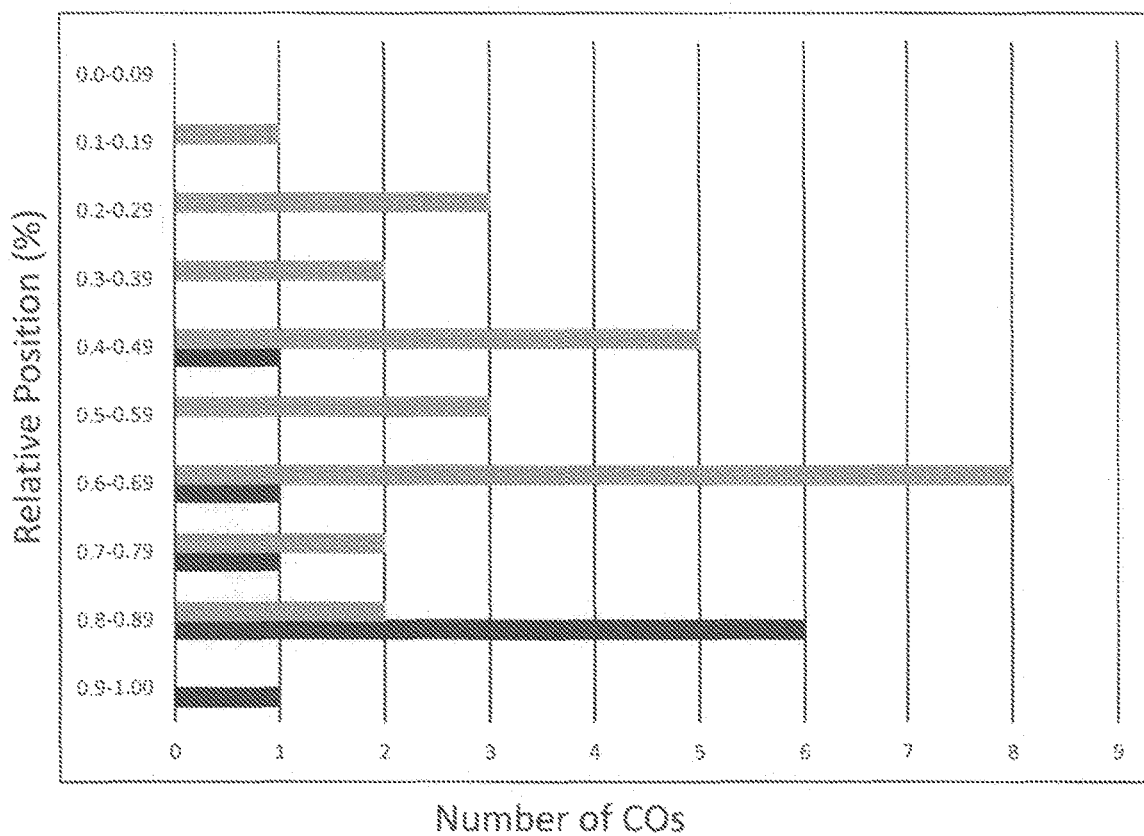
FIG. 6 shows a graph of distribution of crossovers involving chromosomes 5M$^g$ #1 and 5D (black bars) and rec5M$^g$ #2 and 5D (grey bars). Numbers on the Y-axis represent the relative chromosomal position (%) of COs from the telomere (bottom; FL 0.9-1.0) to the centromere (top; FL 0.0-0.09) and the number on the X-axis represents the number of crossovers observed. Recombinant chromosomes used for calculating crossover distribution are presented in FIG. 10A and FIG. 10B.
Figure 7:
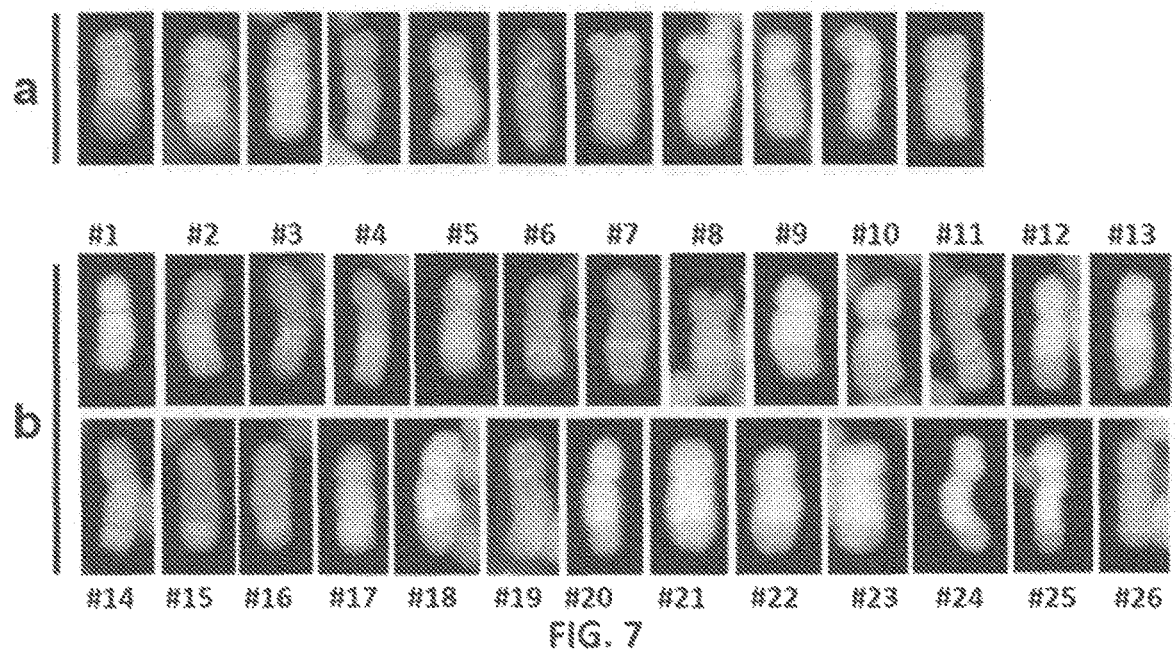
FIG. 7 show images of recombinants involving chromosomes 5M$^g$ #1 or rec5M$^g$ #2 and 5D recovered in the progenies of plants double monosomic for chromosomes 5M$^g$ #1 and 5D (a), or rec5M$^g$ #2 and 5D (b), in the presence of Ph1 gene. Eleven (10.0%, n=110) recombinants were recovered involving chromosomes 5M$^g$ #1 and 5D, and 26 (24.8%, n=106) involving chromosomes rec5M$^g$ #2 and 5D. 5M$^g$ chromatin was visualized in green and 5D chromatin in red.

Next, we compared the distribution of genetic crossovers in 5M$^g$ #1/5D and rec5M$^g$ #2/5D chromosome combinations (FIG. 6). We also determined the frequency of homoeologous recombination using GISH analysis on mitotic metaphase chromosomes in derived progenies (FIG. 7). In the strictly homoeologous chromosome combination of 5M$^g$ #1/5D, genetic crossovers occurred in the distal half of the long arms with highest frequencies in fraction length of 0.80-0.89% from the centromere (fraction length of centromere is zero) (FIG. 6). In the rec5M$^g$ #2/5D combination, homoeologous recombination shifted to homoeologous crossovers in 0.10-0.80% of fraction length with the highest frequency between 0.60-0.69% of fraction length. Four crossover sites were between 0.10-0.29% of fraction length where recombination is known to be suppressed (FIGS. 6, 7).

Figure 8:
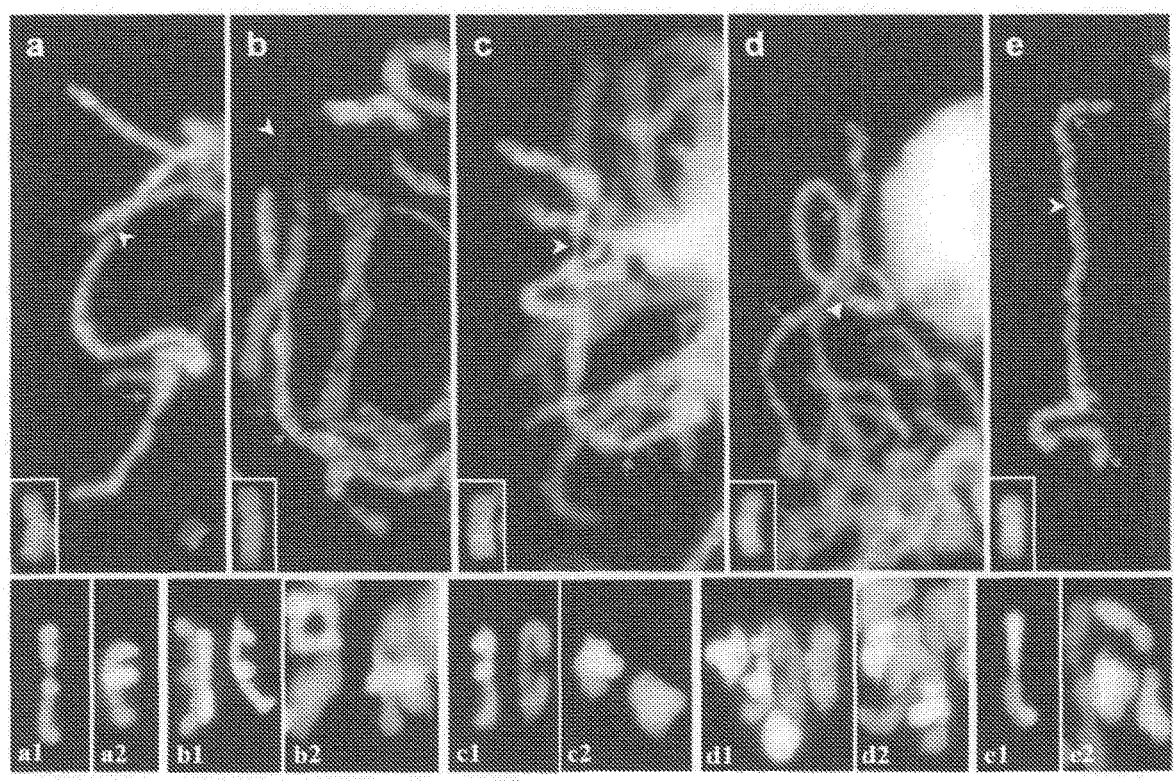
FIG. 8 shows images of synaptic association and meiotic metaphase I pairing involving different 5M$^g$ #2 recombinants and 5D chromosome of wheat. Almost complete synaptic association (>90%) between 5M$^g$ #2 recombinants (R1-R5 in Table 4) and 5D was observed in all cases. Inserts in (a-e) show the different types of 5M$^g$ #2/5D recombinant chromosomes used. a1, b1, c1, d1 and e1 show chiasmata within homologous 5D/5D regions; a2, b2, c2, d2 and e2 show chiasmata within homoeologous 5M$^g$ #2/5D regions. Arrowheads represent the centromeres. Green arrows indicate transition point between 5M$^g$-5D (proximal) 5D-5D distal associations. Red arrows indicate the heterochromatic knobs located on 5DL of wheat. Chromosome 5M$^g$ was labeled with fluorescein and fluoresces green, and the D-genome chromosomes were labeled rhodamine and fluoresce red. Chromosomes of the A and B genomes of wheat were stained with DAPI and fluoresce blue.

To investigate further the question as to how homology at the chromosome end influences the homoeologous recombination frequency, we isolated several recombinants from the progenies of rec5M$^g$ #2/5D plants with different-sized terminal 5DL segments attached to 5M$^g$ #2 ranging in length from 18.7% (recombinant with breakpoint at fraction length 0.81%), 36.6% (fraction length 0.63%), 50.4% (fraction length 0.50%), to 72.0% (fraction length 0.28), designated as R1-R4, respectively (FIG. 8 and Table 4). Our two-color chromosome painting unambiguously distinguished between the different types of recombinants (FIG. 8). The F$_1$ hybrids of each recombinant with CS were developed and synaptic associations and homoeologous recombination between chromosomes rec5M$^g$ #2 and 5D were determined (Table 4 and FIG. 8). In plant R1, we observed complete synapsis in 90.6% (n=39) (Table 4 and FIG. 8). We also analyzed synapsis in the R2-R4 plants. An overall high frequency of >90% synapsis was observed in all recombinants, similar to the level we observed in the P5M$^g$2, which had 5% terminal homology with 5D of wheat (FIG. 8 and Table 4). The results indicate that synapsis is independent of the size of the homologous region and the presence of a homologous region at the tip of a homoeologous chromosome pair is sufficient for a high level of synapsis.

Figure 9:
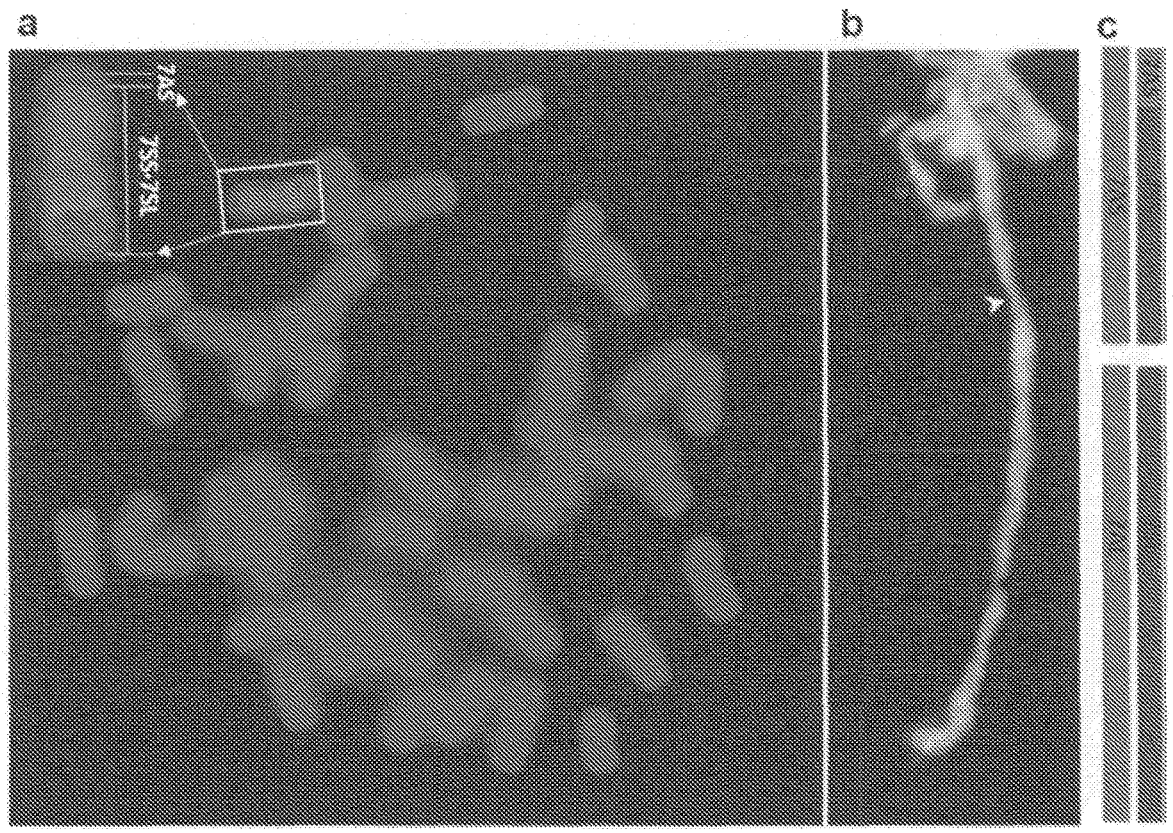
FIG. 9 shows images of a GISH pattern of mitotic metaphase (a) and meiotic pachytene chromosomes (b) of the wheat plants double monosomic wheat-Ae. speltoides translocation chromosome T7SL·7SS-7AS and 7A; b: complete synaptic association (98%, n=100) between 7A (visualized in green) and T7SL·7SS-7AS (red); c: ideogram showing chromosome 7A and T7SL·7SS-7AS. The white arrowhead points to the centromere and the red arrow to 7A-7S translocation point.

To further understand the synaptic behavior of homoeologous chromosome with a region of homology at the tip of one chromosome arm, we analyzed the synaptic behavior of a wheat-*Ae. speltoides* translocation, T7SL•7SS-7AS, consisting of the complete long arm of 7S, most of the short arm of 7S (derived from *Ae. speltoides*), and approximately 10% of the distal segment derived from 7AS of wheat (FIG. 9). We observed almost complete synaptic association (98.0%, n=100) between T7AS•7AL and T7SL•7SS-7AS chromosomes sharing only 10% homology at the 7AS tip, demonstrating that once synapsis is initiated in homologous regions, it also can extend into not only non-homologous but homoeologous regions.

Homoeologous metaphase I pairing is affected by the extent of homology at the terminal regions. Meiotic pairing analysis revealed that with increasing 5D wheat segments from 5% to 19-72% in rec5M$^g$ #2 derivatives, homoeologous metaphase I pairing decreased sharply from 21.7% to values ranging from 4.8-0.8% (FIG. 8 and Table 4). These results indicated that the level of homoeologous metaphase I pairing in different rec5M$^g$ #2/5D recombinants (R1-R4) was inversely proportional to the length of the shared wheat segment. Only P5M$^g$2 and R5 hybrids, both of which had a very small (5%) distal segment of 5DL, showed high homoeologous metaphase I pairing and a high frequency of recombinants in the derived progenies suggesting that 5M$^g$ #2 recombinants with a small wheat segment at the tip have potential for high homoeologous recombination (Table 4). However, this is not a general phenomenon and was not observed in wheat-rye T1BL•1RS-1BS translocations, consisting of the complete long arm of 1B, most of the short arm of 1R (derived from rye, *Secale cereale* L.), and approximately 1-5% distal segment derived from 1BS of wheat (data not shown), implying the presence of a homoeologous pairing promotor gene(s) in chromosome 5M$^g$.

On the other hand, studies of homoeologous synapsis using ZIP1 antibody in wheat-rye hybrids with and without the Ph1 locus found a similar amount of synaptonemal complex components at meiotic prophase I between the two F$_1$ hybrids. A similar number of AtMLH1 (*Arabidopsis* MutL homologue-1, a marker for class-I interfering crossovers) sites in the hybrid plants with and without Ph1 locus were also observed, but homoeologous recombination only occurred in plants without the Ph1 locus.

Cytological Mapping of the Genetic Region Inducing Homoeologous Pairing and Recombination.

The drastic reduction in homoeologous metaphase I pairing and recombination in rec5M$^g$ #2 derivatives indicates that the gene promoting homoeologous metaphase I pairing and recombination may reside in the distal region of 5M$^g$. This gene is deleted in recombinants R1 to R4, where greater than 5% of 5M$^g$ is replaced by the 5DL segment of wheat (Table 4). To further define the genetic region that affects homoeologous metaphase I pairing, we analyzed two additional recombinants R5 and R6 recovered in the progeny of rec5M$^g$ #2/5D with different sized 5D segments (Table 4). In R5, the distal 5% of 5M$^g$ #2 long arm is derived from 5DL of wheat and the distal 45% of short arm is derived from 5DS of wheat. Most of the crossovers were detected between fraction length 0.83-0.15% region of the long arm of rec5M$^g$ #2 (FIG. 6). In R6, the complete short arm as well as the proximal 18% of the long arm and the distal 5% of the long arm of 5M$^g$ #2 are replaced by homoeologous 5D wheat chromatin. We observed 100% synapsis between R5 and 5D chromosomes (FIG. 8e and Table 4). Synapsis between R6 and 5D was not analyzed but it will be expected to be 100%. The frequency of homoeologous recombination in R5/5D hybrids was 24.3% (FIG. 10B) compared to 4.0% (n=100) in the R6/5D hybrids (Table 4). These results indicate the presence of a genetic factor promoting homoeologous recombination in the centromeric 5M$^g$ region encompassing 55% of the proximal short arm and 18% of its long arm. Our results further indicate that, in addition to the homoeologous recombination promoting gene(s), a small region of homology at the terminal end may further increase the level of homoeologous recombination by two-fold.

Chromosome 5M$^g$ can Recombine with Group-5 Chromosomes of Other Wild Wheat Species in the Presence of pH1.

To study homoeologous recombination between 5M$^g$ and other homoeologous group-5 chromosomes from *Aegilops* species, we crossed the DS5M$^g$ #2(5D) substitution line with the wheat-*Ae. searsii* Feldman & Kislev ex K. Hammer DS5S$^s$(5D) substitution line. Surprisingly, 9.0% (n=100)

metaphase I pairing was observed between homoeologous chromosomes rec5M$^g$ #2 and 5S$^s$ and 6.7% (n=56) wheat-*Ae. searsii* recombinants were recovered in the derived progenies (FIG. 11A-C). Other alien chromosomes were surveyed for the presence of homoeologous metaphase I pairing promotor(s) similar to that of chromosome 5M$^g$. Chiasmate metaphase I associations and recombination frequencies were determined in progenies derived from the cross DS5S$^s$(5D)×CS. We observed no chiasmate metaphase I associations (0.0%, n=120) or recombinants (0.0%, n=56) between chromosome 5S$^s$ and 5D (FIG. 11D-E). These results also demonstrate that the double monosomic condition of chromosome 5D with other group-5 alien chromosomes did not affect homoeologous recombination. Likewise, the analysis of chiasmata metaphase I pairing in the F$_1$ between DS7M$^g$(7D)/CS, where 7M$^g$ and 7D are in double monosomic condition, revealed only 0.4% homoeologous metaphase I pairing (n=246) (FIG. 11D-E).

In the F$_1$ hybrid between DS5M$^g$ #1(5D) and rye, we detected homoeologous metaphase I pairing of 1.5% (n=130) between 5M$^g$ #1 and one of the rye chromosomes, most likely 5R. Homoeologous metaphase I pairing between 5M$^g$ #1 and one of the wheat chromosomes, most likely 5A or 5B as well as wheat-wheat associations were also detected (FIG. 12). In addition, homoeologous metaphase I pairing between one rye chromosome and one wheat chromosome was frequently observed (3.8%, n=130) (FIG. 12). Apart from 5M$^g$ #1-rye chromosome association, the 3.8% wheat-rye homoeologous metaphase I pairing frequency observed in this study is much higher than those reported previously, where the frequency of chromosome association at MI between wheat and rye was about 0.1%.

We also observed homoeologous metaphase I pairing at 3.4% (n=114) between chromosome 5M$^g$ and chromosome 5D of wheat in F$_1$ hybrids between wheat and *Ae. geniculata*. Chiasmate associations between U-genome, M-genome, and wheat chromosomes were observed at high frequency (FIG. 13). This is additional evidence of the presence of homoeologous pairing promotor gene(s) on chromosome 5M$^g$.

CONCLUSIONS

Recombination between cultivated and alien chromosomes limits the transfer of novel traits from wild relatives to wheat, because Ph1 suppresses homoeologous recombination between wheat and its wild relatives. In this study, we identified homoeologous recombination between the chromosomes 5M$^g$ of *Ae. geniculata* and 5D of wheat, as well as group-5 chromosomes of wild wheat relatives, in plants where Ph1 was fully active. This demonstrates that chromosome 5M$^g$ harbors genetic factor(s) that suppresses the homologous recombination in wheat, or otherwise promote homoeologous recombination Further cytogenetic analysis, with varying 5M$^g$/5D recombinants, indicated that the homoeologous recombination promoting factor(s) may be located in the proximal region of chromosome 5M$^g$. Interestingly, higher frequency of homoeologous recombination and recombination at pericentromeric region were observed between chromosome 5M$^g$ #2 and 5D of wheat as compared with those of between 5M$^g$ #1 and 5D, is caused by a small terminal region on 5M$^g$ #2 derived from 5D. Chromosome 5M$^g$ of *Ae. geniculata* is of particular interest as it harbors the leaf rust and stripe rust resistance genes, Lr57 and Yr40. We have recovered several 5M$^g$/5D novel recombinants that, together with the previously identified recombinants, will also be useful in the fine mapping Lr57, Yr40, and Sr53.

We observed a higher frequency of homoeologous recombination in the pericentromeric region between chromosome 5M$^g$ #2 and 5D compared to 5M$^g$ #1/5D combination, which is caused by a small terminal region of 5DL homology present in chromosome 5M$^g$ #2. The recombinants obtained in this study will be useful resource for wheat improvement.

Example 2

Proof of concept for enhancing homoeologous recombination between wheat and alien chromosomes was explored.

In the general approach, the disomic substitution DS5M$^g$ (5D) line (TA6675) is first crossed with the homozygous ph1b stock. The TA6675 line contains 20 pairs of wheat chromosomes and chromosome pair 5M$^g$ from *Ae. geniculata* substituting for chromosome 5D of wheat. The F1 of the first cross will be heterozygous for chromosome 5M$^g$/5D and Ph1/ph1b. Separately, a homozygous ph1b stock is also crossed with plants homozygous for the target alien chromosome(s). The F1 plants from this cross will be heterozygous for Ph1/ph1b and the target alien chromosome(s). After intercrossing both F1 s, genotypes will be selected that are homozygous for ph1b/ph1b and heterozygous for chromosomes 5M$^g$/5D and the target alien chromosome(s).

For determining the efficiency of this novel strategy, we tested its efficacy for promoting homoeologous recombination of wheat chromosomes with two rye and *Thinopyrum intermedium* RobTs. Our new strategy for enhancing homoeologous recombination between wheat and alien chromosomes derived from wheatgrass (*Thinopyrum intermedium*) and rye is outlined in FIG. 14. First, the homozygous ph1b stock was crossed with the disomic substitution line DS5M$^g$(5D) (TA6675) (top left) to yield progeny that were heterozygous for chromosome 5M$^g$/5D and Ph1/ph1b (middle left). In *Th. intermedium*, Wsm3 is present on the 7S #3L arm in the form of a RobT T7BS•7S #3L (top right). The H21 gene is present on 2RL rye arm in the wheat-rye Robertsonian translocation (RobT) chromosome T2BS•2RL (top right). All these wheat-alien introgression lines were crossed with the ph1b stock (top right). The F1 plants from this cross were heterozygous Ph1/ph1b and for the alien RobT (middle right).

The F1s from each cross were then intercrossed (middle). In these genotypes homoeologous recombination was seen to occur at a higher frequency and also in proximal chromosome regions where recombination is usually suppressed resulting in alien gene transfers as depicted (Bottom panel). Because the recombinant chromosomes carry smaller amount of alien chromatin with the target gene, they are more likely to be agronomically useful.

The resulting plants were selected that are homozygous for ph1b, and heterozygous for 5M$^g$ and the wheat alien transfer.

Using this approach, a 2% to 4% frequency of induced recombinants were obtained for Wsm3 and 4.3% frequency of recombinants were obtained for H21. Unexpectedly, for Wsm3 this is a up to a 50 times higher frequency of induced recombinants compared to using the ph1b mutant alone. This novel strategy greatly enhances the efficiency of transfer of agronomically useful traits from distantly related species belonging to the tertiary gene pool into wheat. The method also allows the transfer of genes that are located in proximal chromosome regions were recombination is usually suppressed (and previously not feasible).

The invention claimed is:

1. A method of inducing homoeologous recombination in wheat breeding, said method comprising:
   providing a wheat starting stock that comprises chromosome 5M$^g$ comprising a homoeologous recombination promotor gene from *Ae. geniculata* (Hpp-5M$^g$) and at least one chromosome bearing a pairing (Ph) gene which is not functioning;
   providing a source plant capable of crossbreeding with wheat and comprising one or more target genes for recombination with one or more wheat chromosomes;
   crossing said wheat starting stock with said source plant;
   selecting progeny from said crossing that comprises a chromosome comprising one or more of said target genes transferred in a homoeologous recombination event during said crossing, wherein said progeny is homozygous for ph1b/ph1b, and heterozygous for chromosome 5M$^g$/5D, and comprises a recombinant chromosome comprising one or more of said target genes; and
   crossing said progeny with a plant capable of crossbreeding with wheat, wherein one or more of said target genes is transferred in a second homoeologous recombination event during said crossing of said progeny,
   wherein the frequency of said second homoeologous recombination event is twenty-five times greater than recombination of said target gene when crossed with a wheat starting stock in the absence of said 5M$^g$ chromosome.

2. The method of claim 1, wherein said at least one chromosome bearing a pairing (Ph) gene which is not functioning in said starting stock, comprises the mutant homoeologous-pairing allele ph1b.

3. The method of claim 1, wherein said starting stock is heterozygous for Ph1/ph1b.

4. The method of claim 1, wherein said starting stock is heterozygous for chromosome 5M$^g$/5D.

5. The method of claim 1, wherein said chromosome 5M$^g$ is a recombinant chromosome comprising one or more translocated wheat genes in distal regions of said chromosome, provided that said chromosome retains one or more native homoeologous pairing promotor gene(s) from 5M$^g$ of *Ae. geniculata*.

6. The method of claim 1, wherein said starting stock is capable of serving as a parent for breeding stable wheat cultivars.

7. The method of claim 1, wherein said wheat starting stock is a *Triticum aestivum* background.

8. The method of claim 1, wherein said source plant is heterozygous from said one or more target genes.

9. The method of claim 1, wherein said source plant is a different species from said wheat starting stock.

10. The method of claim 1, wherein said source plant is a wheat cultivar.

11. The method of claim 1, wherein said source plant comprises a functional Ph1 allele.

12. The method of claim 1, wherein said source plant comprise at least one chromosome bearing a pairing (Ph) gene which is not functioning.

13. The method of claim 12, wherein said at least one chromosome bearing a pairing (Ph) gene which is not functioning, comprises the mutant homoeologous-pairing allele ph1b.

14. The method of claim 13, wherein said source plant is heterozygous for Ph1/ph1b.

15. The method of claim 1, wherein said target gene transferred during said second homoeologous recombination event is located in a region of the chromosome proximal to the centromere.

16. The method of claim 1, wherein a plurality of genes are transferred in said second homoeologous recombination event.

17. The method of claim 1, comprising two or more of said second recombination homoeologous events.

18. The method of claim 1, wherein the frequency of second homoeologous recombination events in said crossing is at least 3%.

19. The method of claim 1, further comprising collecting the progeny seed from said crossing and growing said seeds, thus producing progeny plants expressing said one or more of said target genes.

20. The method of claim 19, wherein said one or more target genes confer a desirable trait to said progeny plants.

21. A method of inducing homoeologous recombination in wheat breeding, said method comprising:
   crossing a wheat starting stock and a source plant capable of crossbreeding with wheat and comprising one or more target genes for recombination with one or more wheat chromosomes, wherein said wheat starting stock comprises chromosome 5M$^g$ comprising a homoeologous recombination promotor gene from *Ae. geniculata* (Hpp-5M$^g$) and at least one chromosome bearing a pairing (Ph) gene which is not functioning;
   selecting progeny from said crossing that is homozygous for ph1b/ph1b, and comprises a chromosome comprising one or more of said target genes transferred in a homoeologous recombination event during said crossing; and
   crossing said progeny with a plant capable of crossbreeding with wheat, wherein one or more of said target genes is transferred in a second homoeologous recombination event during said crossing of said progeny,
   wherein the frequency of said second homoeologous recombination event is twenty-five times greater than recombination of said target gene when crossed with a wheat starting stock in the absence of said 5M$^g$ chromosome.

22. The method of claim 21, wherein said target gene transferred during said second homoeologous recombination event is located in a region of the chromosome proximal to the centromere.

23. The method of claim 21, wherein said at least one chromosome bearing a pairing (Ph) gene which is not functioning in said starting stock, comprises the mutant homoeologous-pairing allele ph1b.

* * * * *